United States Patent [19]
Quinn et al.

[11] Patent Number: 4,941,359
[45] Date of Patent: Jul. 17, 1990

[54] ARTICULATING FLEXURE TEST FIXTURE

[75] Inventors: George D. Quinn, Watertown; Raymond L. Goulet, Norwood, both of Mass.

[73] Assignee: The United States of America as represented by the Secretary of the Army, Washington, D.C.

[21] Appl. No.: 306,005

[22] Filed: Feb. 2, 1989

[51] Int. Cl.$^5$ .................................................. G01N 3/20
[52] U.S. Cl. .................................................... 73/851
[58] Field of Search ......................... 73/851, 849, 856

[56] References Cited

FOREIGN PATENT DOCUMENTS 1379690  3/1988  U.S.S.R. ................................ 73/849

OTHER PUBLICATIONS

"MTL Flexure Fixtures", G. D. Quinn, May 1985; Revised Sep. 1986.
"Reduction of Errors in Ceramic Bend Tests", R. G. Hoagland et al., Journal of The American Ceramic Society, vol. 59, No. 5-6, May-Jun. 1976.
"Requirements for Flexure Testing of Brittle Materials", Francis I. Baratta, Army Materials and Mechanics Research Center Technical Report 82-20, Apr. 1982.
Bailey, R. T. Measurement of Strength . . . Bodies, Trans. & J. Br. Ceram. Sc.(GB), vol. 71, No. 8, Dec. '72, pp. 272-277.

Primary Examiner—Jerry W. Myracle
Attorney, Agent, or Firm—Richard J. Donahue

[57] ABSTRACT

An articulating fixture for the flexure testing of ceramics, having a lower structure for supporting the bottom of a specimen to be tested and an upper structure for placing a load into the top surface of the specimen. Each such structure includes at least one articulated cooperating assembly which allows rotation in the direction of the surface of the specimen whereby when the specimen is twisted, it will adapt to the twist and still properly apply the load to the specimen. In one arrangement, each of the structures includes two lines of pressure provided by two loading pins so that there are four such points in the fixture. In another arrangement, the upper structure includes one line of pressure provided by one loading pin, and the bottom structure includes two lines of pressure provided by two loading pins so that there are three such points in the fixture. The assembly for the lower structure includes a lower support cradle having an arcuate groove extending in the same direction as the specimen, and a swivel bearing support having a convex arcuate surface which mates with the surface of the groove so that the cradle and swivel bearing support are slidable with the swivel bearing support rotating within the groove to accommodate twisted specimens. The loading pin may contact the swivel bearing support on one side and the specimen at another side opposite the first side.

5 Claims, 2 Drawing Sheets

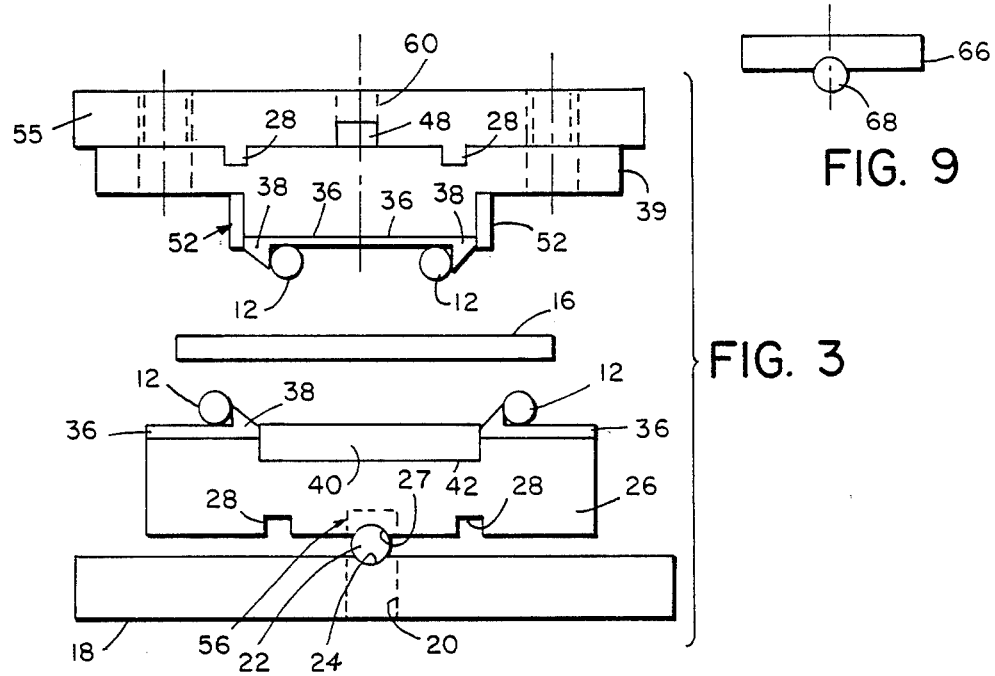
FIG. 9
FIG. 3
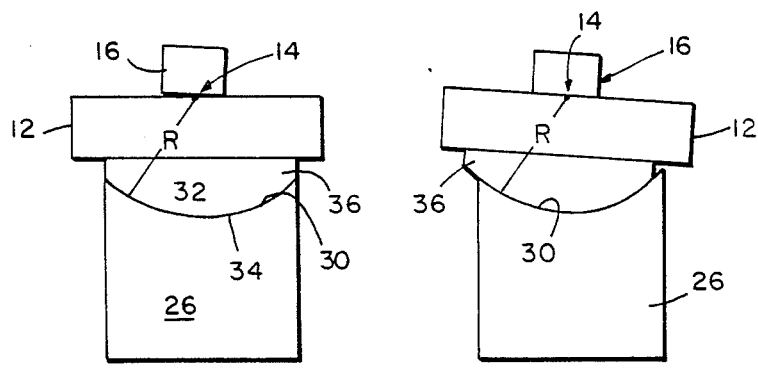
FIG. 4
FIG. 5
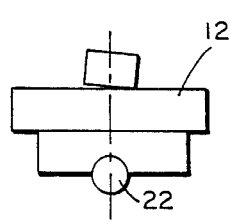
FIG. 6
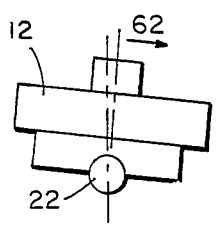
FIG. 7
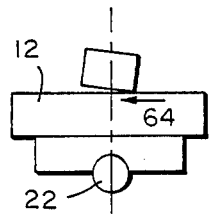
FIG. 8

ARTICULATING FLEXURE TEST FIXTURE

The invention described herein may be manufactured, used and licensed by or for the Government for Governmental purposes without the payment to us of any royalty thereon.

BACKGROUND OF THE INVENTION

This invention relates to an apparatus to perform the four point flexure mechanical test for high performance ceramics at ambient conditions. The four point flexure test, also known as the modulus of rupture or bend strength test, is used to measure the tensile strength of a ceramic. The flexure test can be used for quality control or design data generation purposes. For either application (but especially for design data), it is important to perform the test in as error-free a fashion as possible. This aspect is of increasing importance as new advanced or high performance ceramics are employed in structural applications. Considerably greater care must be exercised in testing these materials as opposed to earlier methods developed for whitewares or refractory insulation.

In the four point flexure test, a prismatic specimen (usually rectangular or square) is placed in a jig or fixture which has four knife edges or load application bearings to apply load to the specimen. These loading points are arranged in a symmetrical fashion and create bending stresses and strains in the ceramic specimen. It is essential that these loading points apply even, uniform loadings to the specimen. This is generally not a problem with well-machined ceramic specimens, but can be a problem with as-fired or sintered ceramic specimens, that are slightly irregular geometrically. The specimen is loaded to failure and simple beam theory is used to calculate the maximum tensile strength in the specimen at the instant of failure. The strength numbers will be accurate and precise only if the loading points apply even, uniform loads to the specimen. A standard procedure for flexure testing has been developed: US Army Military Standard MIL-STD 1942 (MR) dated 21 November 1983 and entitled "Flexural Strength At High Performance Ceramics At Ambient Temperature." This method was developed to create a standard practice that will create error-free test results suitable for high strength, brittle ceramics.

SUMMARY OF THE INVENTION

A major object of the present invention is to reduce testing time, eliminate errors and to lower costs, particularly when the specimen is twisted or bent.

A fully articulating fixture has long been of interest to the U.S. Army Material Technology Laboratory (MTL) and other laboratories. It was important, however, that the Army MIL-STD 1942 (MR) be completed before any fixturing was to be designed. Immediately following publication of the standard, work was started on an apparatus for testing well-machined specimens to be in compliance with the flexure test standard. This work has been completed and a non-articulating jig has been constructed and used reliably by several groups at the Army Material Technology Laboratory since 1983. This earlier jig had the feature that the load bearings were free to rotate in order to relieve unwanted constraints in the specimen due to specimen expansion and contraction.

The present invention relies on a so-called "cradle" concept which also permits articulation of the test fixture, as explained more fully below.

Evaluation of the apparatus commenced using Coors AD-999 Alumina as a good material for strength evaluation, since a vast amount of flexure data was already in existence on well-machined specimens used on the simpler nonarticulating jig. The new jig, however, accurately tests well-machined as well as twisted specimens.

The present invention reduces errors significantly during testing, and reduce testing time, and thus reduce costs as compared to predecessor jigs. It is used to determine fracture strength of brittle materials. It significantly aids in reducing errors during flexure testing of brittle materials and thus improves the state of the art. The articulating configuration is less complicated than other fixtures. It also produces more reliable data with less time required per testing of brittle materials.

The novel fixture has been used to validate the articulating scheme at the U.S. Army Material Technology Laboratory. The testing confirmed that the fixture can and does articulate for a twisted specimen. The advantages over existing systems are that the invention reduces testing time, errors and costs, especially when testing twisted specimens.

The apparatus described in this specification was designed to be in accordance with the MIL STD 1942 (MR); however, the apparatus design is applicable to all flexure testing of ceramics. The apparatus provides complete articulation, is extremely accurate and permits fast alignment. The fixture is designed to function equally well with ideal prismatic machined specimens, or less well-machined or as-fabricated specimens. Such specimens often have minor warpages or irregularities, such that when they are used with conventional flexure fixtures, uneven loading results. This, in turn, causes significant experimental error. For example, as little as a 1 degree twist (or warpage) in a ceramic specimen can create large (5-20%) experimental errors. The new fixture minimizes spurious off-axis bending, torsional loading, and other errors associated with testing of perfect as well as imperfect ceramic specimens. Analysis of such errors is explained in the aforementioned U.S. Army Military Standard 1942 (MR); and Army Materials and Mechanics Research Center Technical Report 82-20, "Requirements for Flexure Testing of Brittle Materials," Francis Baratta, April 1982.

A very simple modification is made to convert the jig to a three point flexure configuration, which is also commonly employed to measure the strength of ceramics. This modification is interchangeable and permits one fixture set to be used for either three or four point loading.

Alternative designs have been devised by others to deal with as-sintered or warped specimens. See, for example, R.G. Hoagland, C.W. Marschall, and W.H. Duckworth, "Reduction of Errors in Ceramic Bend Tests," J. Am. Ceramic Soc., Vol.59 No. 5-6 (1976). However, the present design is a major improvement thereover. It includes fewer parts, is of simpler construction, is easier set-up and utilized, and provides faster, more efficient testing.

BBIEF DESCRIPTION OF THE DRAWINGS

FIG. 3 is an exploded view of the present invention showing certain details thereof.

FIG. 4 is a schematic end view of the articulating fixture of the present invention with the specimen misaligned.

FIG. 5 is a schematic end view of the articulating fixture of the present invention with the specimen aligned.

FIG. 6 is an end view of an articulating fixture having a twisted specimen thereon.

FIG. 7 is an end view of the articulating fixture in which the fixture has articulated to accommodate the twisted specimen without sliding over the load bearing as a fixture articulates.

FIG. 8 is an end view of the articulating fixture in which the twisted specimen slides over the load bearing as the fixture articulates.

FIG. 9 is a side view of an insert used to convert the articulating fixture to a three-point node of loading.

DETAILED DESCRIPTION OF THE PREFERRED EMBODIMENTS

Figure 1:
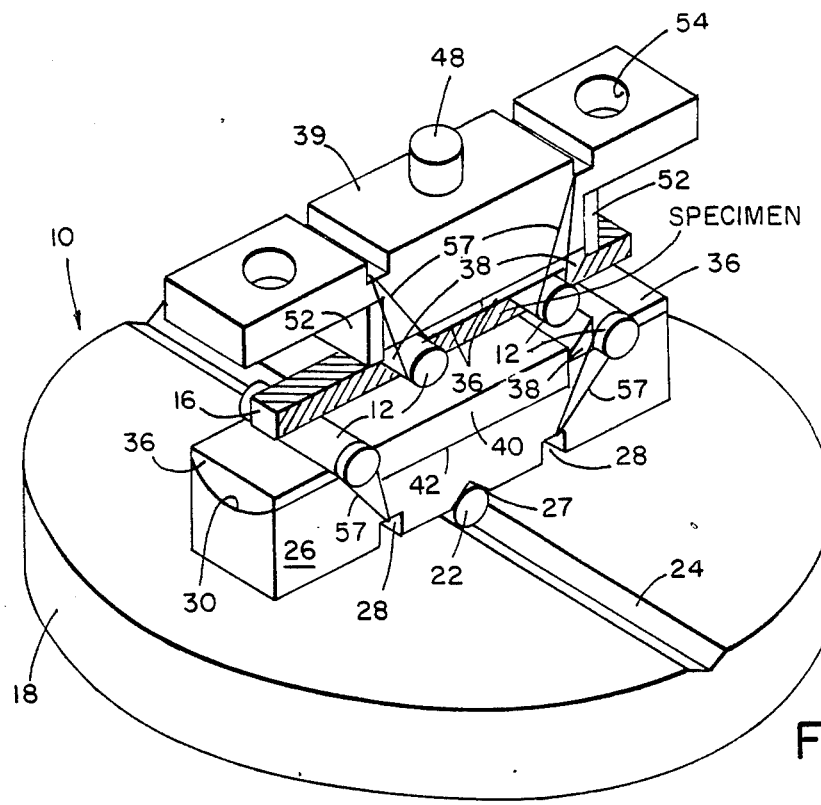
FIG. 1 is a perspective view of the present invention used with a prismatic specimen.
Figure 2:
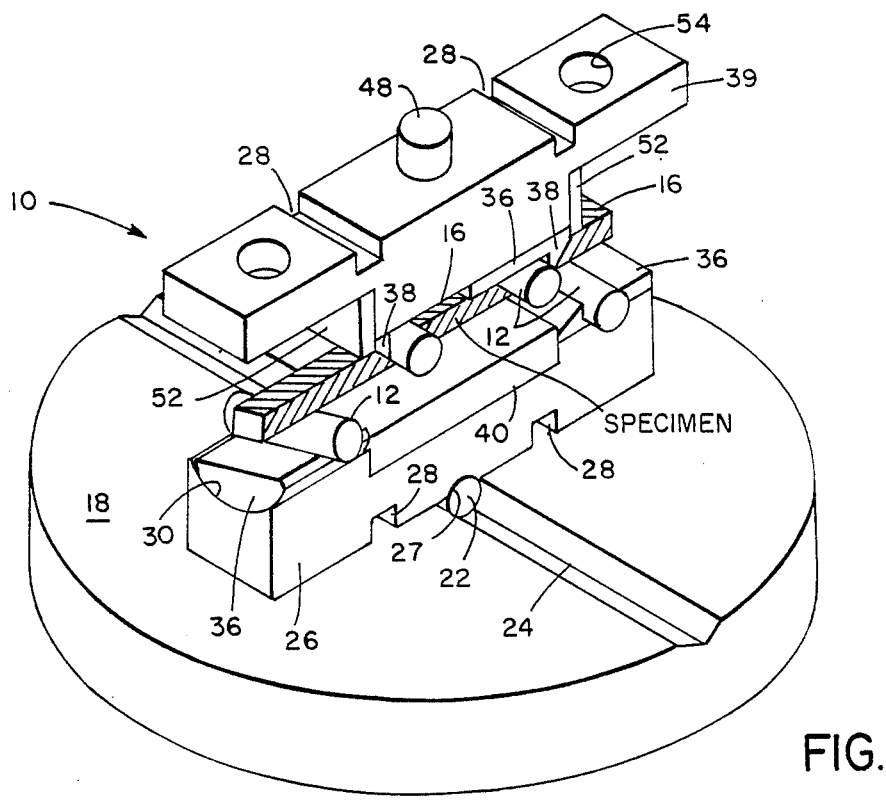
FIG. 2 is a perspective view of the present invention used with a twisted specimen.

This jig 10 is unique in its method of articulation and is shown in FIGS. 1 and 2. It relies upon a new arrangement or assembly called "cradle" articulation, shown in a schematic view in FIG. 3, which is a side view of a portion of the fixture 10. This singular design allows each loading pin 12 to rotate about an axis 14 (see FIGS. 4 and 5) coincident with the center of the matching face of the specimen 16, without the use of complex roller bearing assemblies. This is an important aspect of the apparatus. The remainder of the jig includes a lower adaptor plate 18, having hole 20 for the locating pin used in three point testing. Hole 20 also serves to permit centering of the lower adaptor plate 18 relative to the upper adapter plate 55 during initial setup and alignment. A pivot roller 22 sits in a V-shaped groove 24. The bottom of a lower support cradle 26 has a V-shaped groove 27 in its bottom so that it may seat on top of the pivot roller 22. This lower support cradle 26 has two grooves 28 which are used to locate rubber bands 57 that hold load bearings 12 in place. At the upper end of the lower support cradle 26 there is an arcuate groove 30 which is a radius 32 of a circle as shown in FIGS. 4 and 5. Within each groove 30 and having a bottom with a matching convex-like lower surface 34 is a swivel bearing support 36 which is movably seated in the groove 30 of the support cradle 26 so that the matching groove surface and the matching convex surface of the swivel bearing support 36 may slide with respect to each other and provide for the swivel bearing supports 36 to move within the groove 30 in the lower support cradle 26.

Each swivel bearing support 36 has a projecting point formed by a triangular flange 38 against which the loading pins 12 engage. A spacer 40 is provided in a cut out 42 in the top surface of the lower support cradle 26. As shown in FIGS. 1, 2 and 3 the specimen 16 rests on the two lower loading pins 12 and thus in the event the specimen is twisted, the swivel bearing support 36 which supports the particular loading pin 12 which lies against the surface of the twisted end, may swivel so that the axis of the pin becomes parallel with the lower surface of the twisted specimen end as shown in FIGS. 2 and 5.

The upper support cradle 39 is of similar construction and has a locating pin 48 to center upper support cradle 39 on upper adapter plate 55. Upper support cradle 39 has an arcuate groove into which sit two swivel bearing supports 36, which are held in position by two end stops 52. The two upper swivel bearing supports 36 have projecting points formed by a triangular flange 38 against which the loading pins 12 engage. Loading pins 12 and the swivel bearing supports 36 are held in place by rubber bands 57 which loop through grooves 28, as shown in FIGS. 1–3.

FIG. 4 illustrates the possible uneven (point and not line) loading that can occur when an as-fired or twisted specimen is put into the fixture 10. The fixture 10 is designed to automatically rectify this undesirable situation and to articulate so that the load bearings 12 come into uniform line loading on the surface of specimen 16 without the specimen 16 shifting, as illustrated in FIG. 5. This is the ideal mode of loading assumed in the strength analysis. Lowering the crosshead (not shown) of the universal testing machine provides a force which creates a moment to cause the swivel bearing supports 36 to rotate, eliminating the uneven loading. If the swivel bearing supports 36 are polished, and lubricated with graphite, there will be negligible resistance to such articulation. Four such swivel bearing supports 36 provide complete articulation at all loading points, but in practice one can be fixed in place, since the remaining three will have sufficient degrees of freedom to accommodate the specimen 12. Thus the cradle system will self-align the entire apparatus as shown in FIG. 2.

This cradle design (FIG. 4) also eliminates any off-center movement sideways, as shown by arrow 62, in FIG. 7 of the specimen 12 during articulation. This is a key point since a sideways sliding across a loading roller bearing would be resisted by frictional forces as depicted by arrow 64 in FIG. 8. These forces would resist self alignment causing alignment errors, and thus errors in the test result. Furthermore, such sideways movement would tend to shift the specimen location in the fixture causing a possible misalignment as shown in FIG. 7. No previous fixture employs the new cradle design, which relies upon the axis of rotation (or articulation) 14 being coincident with the center of the specimen face.

An important feature of the invention is that the load bearings 12 are free to rotate to relieve constraints associated with expansion or contraction of the specimen during loading. Rubber bands 57 hold the assembly together, but also hold the load bearings 12 against locating shoulders 38. These rubber bands 57 also permit the lower bearings 12 to roll outward when the bottom surface of specimen 16 expands during testing. Rubber bands 57 also permit the upper bearings 12 to roll inwardly as the top surface of the specimen contracts during testing. This rolling action of load bearings 12 is an essential feature of a fixture and has been previously used in the earlier non-articulating fixture developed at MTL, and is also shown in the Hoagland et al article mentioned earlier.

The major feature of the fixture 10 is its ability to successfully test a less than perfect rectangular or square specimen 16, but its total usefulness is far more reaching than this. Because this jig is fully articulating and self-aligning, it can test all specimens with no lengthy set-up procedures. The implications are as follows: first, testing may now be accomplished in significantly shorter time periods; and second, operator "carefulness" has much less effect upon the quality of the flexure test. The fixture can test will machined or as-fired or warped specimens equally well. It therefore is capable of replacing all previous fixturing.

The fixture of Hoagland et al identified above represents the state of the art in current articulating fixture technology. The jig was well designed and thoroughly evaluated; however the new fixture offers significant advances thereover. The Hoagland et al apparatus is a cumbersome one. Its aligning system and large numbers of components make it difficult and slow to use. It is difficult to insert or extract specimens therein. In contrast, the fixture of the present invention is uncluttered and has far fewer moving parts. A one time only aligning system is used before testing and then is removed. The fixture permits easy loading and unloading of specimens. The most important advance of the apparatus described herein, however, is its "cradle" articulation.

As stated earlier, this system allows the specimen to automatically push the cradle into proper position during loading with no "sideways" motion of the specimen, as observed in FIG. 7. This is particularly important. The Hoagland et al apparatus does not possess this key feature. Rather, the latter apparatus uses dowel pins rotating on plates or V-grooved blocks to provide this articulation. If friction at the specimen face is great, the specimen will stay in contact with the loading pin and articulation will pull the specimen off-center as shown in FIG. 7. Alternatively, if friction is low at the specimen face, the specimen may stay centered. However, the sliding friction will resist self-aligning of the jig as seen in FIG. 8. Thus, only the jig described herein allows proper centering and self-alignment simultaneously. Tests which were carried out fully support this conclusion. These tests were verified with the specimen and fixtures deliberately misaligned. The fixture in every instance articulated perfectly. Test results agreed exactly with results for well machined specimens on precision non-articulating fixtures.

The apparatus is intended to be used in a universal testing machine. The particulars of the design are as follows. Loads are applied to the specimen via commercially available, hardened steel dowel pins 12 which rest upon the swivel bearing supports 36. The support cradles 26 and 39 and swivel bearing supports 36 are made of Maraging 250 steel (or equivalent) which has sufficient hardness (HRC 30) in an annealed, as-machined state so that heat treating is unnecessary. High contact stresses from the load bearings could permanently deform or damage softer grade materials. This grade steel is also oxidation and corrosion resistant which is important for maintaining tolerance requirements.

A pivot roller 22 permits articulation of the lower support cradle 26 to give even load application on the two lower load bearings 12, as seen in FIG. 3. The lower adaptor plate 18 serves to locate the roller 22 (and in turn the support cradle 26) and conform to the loading platform of the universal testing machine. The upper support cradle 39 bolts rigidly to the upper adaptor plate 55, which in turn is rigidly attached to the crosshead of the universal testing machine. A short ¼" diameter pin 48 aligns the upper support cradle 39 to the upper adaptor plate 55. The upper support cradle has bores 54 therein, to accommodate mounting screws (not shown).

Apparatus alignment requires concentricity of the upper and lower adaptor plates 55 and 18, respectively. This can be accomplished using a long straight ¼" diameter rod passed through centering holes 20 and 60 in the adaptor plates 18 and 55, respectively. The only other alignment necessary is to insure that the upper and lower support cradles are parallel. The steps taken to insure proper alignment may vary depending upon the particulars of the universal testing machine hardware. The system is aligned only once during the initial setup.

A simple insert 66 as shown in FIG. 9 can be placed between the upper swivel cradles 36 to convert this apparatus to a 3-point flexure test jig. The same elastic bands serve to hold the insert 66 and loading pin 68 in position. In this mode the pivot roller 22 of the lower support cradle 26 is removed and the lower support cradle is inserted directly into the lower adaptor plate 18 via the addition of a short 0.250 inch diameter pin (not shown) inserted into holes 20 and 56. Thus, three point flexure testing may be performed with extreme ease of conversion and testing.

The apparatus as described has been developed completely for size "B" specimens of US Army MIL-STD 1942 (MR), which are $3.0 \times 4.0 \times 45$–50 mm in size. The fixture spans (distances between support and loading rollers) are 40 and 20 mm. The same design features can be used for alternative specimen sizes and fixture spans, however.

In general, the apparatus described herein permits error free testing for well machined, as-fired or sintered specimens, it facilitates faster and more efficient testing of such specimens.

It should be understood that various changes and modifications to the embodiments of the invention as described hereinabove will be apparent to those skilled in the art. Such changes can be made without departing from the spirit and scope of the invention and without diminishing its attendant advantages. It is therefore intended that such changes and modifications be covered by the following claims.

We claim:

1. An articulating fixture for the three-point flexure testing of ceramics, comprising:
    lower means for supporting the bottom of a specimen to be tested and arranged to provide line contact near the two ends of the specimen;
    upper means for placing a load onto the top surface of a specimen, said upper means including one line of pressure and said bottom means including two lines of pressure so that there are three loading points in the fixture; and
    each of said means including at least one articulated cooperating assembly which allows rotation in the direction of the contacting surface of the specimen whereby when the specimen is twisted, said fixture will adapt to the twist and still properly apply the load to the specimen;
    the assembly for said lower means including a lower support cradle having an arcuate groove extending in the same direction as the specimen, and a swivel bearing support having a convex arcuate surface which mates with the surface of the groove so that the cradle and swivel bearing support are slidable with the swivel bearing support rotating within the groove to accommodate twisted specimens.

2. An articulating fixture for the three-point flexure testing of ceramics as defined in claim 1, wherein
    each assembly includes a loading pin which contacts the swivel bearing support on one side and the specimen at another side opposite the first side.

3. An articulating fixture for the four-point flexure testing of ceramics, comprising:

lower means for supporting the bottom of a specimen to be tested and arranged to provide line contact near the two ends of the specimen;

upper means for placing a load onto the top surface of a specimen and arranged to provide line contact at two spaced locations which are aligned to be between the line contact provided for the lower means whereby four point contact with the specimen is provided; and each of said means including at least one articulated cooperating assembly which allows rotation of the portion which supports the specimen about a radius having its center at the surface thereof which is closest to the specimen and located midway between the ends of such portion whereby when the specimen is twisted, the assembly will adapt to the twist and still properly apply the load to the specimen.

4. An articulating fixture for the flexure testing of ceramics as defined in claim 3, wherein the assembly for the lower means includes a lower support cradle having an arcuate groove extending in the same direction as the specimen, and a swivel bearing support having a convex arcuate surface which mates with the surface of the groove so that the cradle and swivel bearing support are slidable with the swivel bearing support rotating within the groove to accommodate twisted specimens.

5. An articulating fixture for the flexure testing of ceramics as defined in claim 4, wherein each assembly includes a loading pin which contacts the swivel bearing support on one side and the specimen at another side opposite the first side.

* * * * *